(12) United States Patent
Samsoondar et al.

(10) Patent No.: US 7,343,185 B2
(45) Date of Patent: Mar. 11, 2008

(54) MEASUREMENT OF BODY COMPOUNDS

(75) Inventors: James Samsoondar, Cambridge (CA); Duncan MacIntyre, Campbellville (CA)

(73) Assignee: NIR Diagnostics Inc., Campbellville (CA)

( * ) Notice: Subject to any disclaimer, the term of this patent is extended or adjusted under 35 U.S.C. 154(b) by 862 days.

(21) Appl. No.: 10/465,490

(22) Filed: Jun. 18, 2003

(65) Prior Publication Data

US 2004/0015060 A1    Jan. 22, 2004

Related U.S. Application Data

(60) Provisional application No. 60/390,596, filed on Jun. 21, 2002.

(51) Int. Cl.
*A61B 5/00*    (2006.01)
(52) U.S. Cl. .................................. 600/310; 600/309
(58) Field of Classification Search ................ 600/310, 600/316, 322, 323, 309
See application file for complete search history.

(56) References Cited

U.S. PATENT DOCUMENTS

| | | | |
|---|---|---|---|
| 5,137,023 A * | 8/1992 | Mendelson et al. ......... 600/316 |
| 5,308,919 A * | 5/1994 | Minnich ..................... 600/320 |
| 5,361,758 A | 11/1994 | Hall et al. |
| 6,040,578 A | 3/2000 | Malin et al. |
| 6,236,047 B1 | 5/2001 | Malin et al. |
| 6,240,306 B1 * | 5/2001 | Rohrscheib et al. ........ 600/316 |
| 6,365,363 B1 | 4/2002 | Parfenov et al. |
| 2001/0047128 A1 * | 11/2001 | Benni ......................... 600/323 |

FOREIGN PATENT DOCUMENTS

WO    WO 93/16629    9/1993

OTHER PUBLICATIONS

Potts et al., 2002, "Glucose Monitoring by reverse iontophoresis", Diabete/Metabolism Research and Reviews, 18 (Suppl. 1):S49-S53.
Tierney et al., 2000, "Electroanalysis of Glucose in Transcutaneously Extracted Samples", Electroanalysis 12:666-71.

* cited by examiner

*Primary Examiner*—Eric Winakur
*Assistant Examiner*—Etsub D Berhanu
(74) *Attorney, Agent, or Firm*—Wilmer Cutler Pickering Hale and Dorr LLP

(57) ABSTRACT

The present invention provides a method for identifying a concentration of a compound within a part of a subject. The method involves measuring the amount of electromagnetic radiation reflected by, or transmitted through the part with a detector, and using a quantitative mathematical analysis to determine the concentration of the compound in one, or more than one compartment, including a blood, interstitial, cellular, lymph, or bone compartment, of the part. A corrected concentration of the compound may be then determined within a compartment of interest, or a total concentration of the compound may be accurately determined. Preferably, the compound is glucose. From this determination, a clinical condition in a human or animal may be made by correlating the concentration of a measured compound in the compartment of a part of the human or animal to a clinical condition in need of treatment.

3 Claims, No Drawings

MEASUREMENT OF BODY COMPOUNDS

FIELD OF THE INVENTION

The present invention relates to a method of measuring the concentration of a compound in the body of a subject, for example, a human or animal. More particularly, the present invention relates to a method of determining a concentration of a compound in a part of the subject, and optionally, of correlating the measured concentration of the compound to a specific clinical condition or to the propensity for a specific clinical condition.

BACKGROUND OF THE INVENTION

Non-invasive measurement of the concentration of a compound or analyte in a part of a subject, such as the finger, arm or earlobe, may be difficult in cases where there is interfering background absorption of the same, or other analytes, within the body part from non-target compartments. Changes in the volume of the different compartments may also adversely impact on readings obtained for the determination of a compound within a part of the body.

Compartments within tissue of the body may include, but are not limited to the vascular, interstitial, cellular, lymph, connective tissue, and bone compartments. In the case where the interfering background absorption is from the same analyte present in a non-target compartment, then the concentration of the analyte in the compartment of interest may be overestimated. Changes in the volume of different compartments within the light path, may effect the determination of the concentration of the compound In order to determine the total amount of a compound within a body part, the occurrence of the compound within each of the compartments may be required. This may be important in cases where the relative amount of a compound of interest may vary within different compartments over time or as a result of a medical condition.

For example, when the method disclosed in U.S. Pat. No. 5,361,758 (Hall et al.) is used to measure the blood glucose concentration in diabetic patients adhering to an insulin regime, the background glucose concentration in the cells and the interstitial fluid is negligible and does not interfere significantly with the measured plasma glucose concentration. However, any excess glucose in the blood is eliminated through urination, resulting in dehydration of the patient as water is continuously removed from the tissues of the body and from the interstitial fluid. As a result of the decrease in the cellular and interstitial fluid volumes, the effective glucose concentrations in the cellular and interstitial compartments increases. The increase of glucose in non-target compartments can interfere with the measurement of the blood glucose concentration when using non-invasive measurement techniques, such as that disclosed in Hall et al. This overestimation can result in an inaccurate reading of blood glucose levels. The development of a process that is able to determine the concentration of a particular analyte in different compartments of a part of an individual is therefore of importance.

Clinical studies have revealed that the concentration of certain compounds in one particular compartment of a part of a subject, such as the skin, may be used to assess the risk of development of specific medical conditions in that subject. Early detection of these types of risks in a patient permits measures to be taken that may slow or even prevent the onset of these conditions. As an example, it has been determined that elevated concentrations of cholesterol in the skin of an individual is an indication of a risk for coronary disease. Therefore, the development of simple, non-invasive methods for determining the concentration of skin compounds is of importance.

In U.S. Pat. No. 6,365,363, Parfenov et al. describe a method of indirectly measuring the concentration of cholesterol in the skin of a subject by enzymatically oxidizing the cholesterol in a section of the subject's skin and then quantitating the amount of the hydrogen peroxide by-product stoichiometrically formed in this reaction using a second enzymatic reaction. As a complex series of enzymatic reactions are used in this method to indirectly determine the concentration of cholesterol, the method is both costly and prone to error. In addition, the development of a result using this method is time consuming.

In U.S. Pat. Nos. 6,236,047 and 6,040,578, Malin et al. describe a method for determining the concentration of a blood compound using light in the nearinfrared range by analysing diffusively reflecting radiation emerging from the irradiated sample. However, there is no teaching in these patents as to the determination of concentrations of constituents in the various compartments of a part of a subject.

Hall et al. also describe in U.S. Pat. No. 5,361,758 a non-invasive technique for directly measuring the concentration of constituents of blood using light in the near-infrared range. The glucose value is referenced with respect to the blood compartment only and the glucose concentrations obtained using this method may be prone to error arising from changes in the fluid content in other compartments.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to a method of measuring the concentration of a compound in the body of a subject, for example, a human or animal. More particularly, the present invention relates to a method of determining a concentration of a compound in a part of the subject, and optionally, of correlating the measured concentration of the compound to a specific clinical condition or to the propensity for a specific clinical condition.

The present invention provides a method for determining a concentration of a compound in a part of a subject, comprising:

(a) directing electromagnetic radiation (EMR) from the near-infrared spectrum onto the part;

(b) measuring a quantity of EMR reflected by, or transmitted through the part with a detector; and (c) performing a quantitative mathematical analysis of the quantity of EMR using an algorithm that accounts for concentration of the compound within more than one compartment, and the volume of the part; and (d) determining the concentration of the compound in the part.

The present invention provides a method for determining the concentration of a compound in one, or more than one, compartment of a part of a subject, comprising:

(a) directing electromagnetic radiation (EMR) from the near-infrared (NIR) spectrum onto the part;

(b) measuring a quantity of EMR reflected by, or transmitted through the part with a detector; and (c) performing a quantitative mathematical analysis of the quantity of EMR to determine the concentration of the compound in each of the one, or more than one, compartment of the part.

The present invention also provides a method for determining the concentration of a compound in a compartment of a part of a subject, the method comprising the steps of:
(a) directing electromagnetic radiation (EMR) from the near-infrared (NIR) spectrum onto the part;
(b) measuring a quantity of EMR reflected by, or transmitted through the part with a detector; and
(c) performing a quantitative mathematical analysis of the quantity of EMR, using algorithms for the compound within each compartment to determine the concentration of the compound in each compartment within the part, and
(d) calculating the concentration of the compound in the part.

The present invention pertains to a method for determining a corrected concentration of a compound in a compartment of a part of a subject, comprising:
(a) directing electromagnetic radiation (EMR) from the near-infrared spectrum onto the part;
(b) measuring a quantity of EMR reflected by, or transmitted through the part with a detector;
(c) performing a quantitative mathematical analysis of the quantity of EMR using algorithms for the compound within each compartment; and
(d) determining the concentration of the compound in each compartment.

The present invention also provides a method of identifying a clinical condition in need of treatment in a human or animal, the method comprising the steps of:
(a) directing electromagnetic radiation (EMR) from the near-infrared spectrum onto the part;
(b) measuring a quantity of EMR reflected by, or transmitted through the part with a detector;
(c) performing a quantitative mathematical analysis of the quantity of EMR to determine the concentration of the compound in the compartment, wherein the mathematical analysis involves a step of determining a total concentration of the compound in the part, and a step of assigning a fraction of the total concentration to each compartment of the part, and
(d) correlating the concentration of the compound in each compartment to the clinical condition in need of treatment by using a correlation algorithm.

Thye present invention is also directed to a method to determine an algorithm for deriving a compound concentration in a part of a body comprising:
(a) measuring a concentration of the compound in two or more compartments within the part;
(b) directing electromagnetic radiation (EMR) over a set of wavelengths onto the part;
(c) measuring a quantity of EMR reflected by, or transmitted through the part with a detector for each wavelength of the set of wavelengths, to obtain a set of values;
(d) performing a statistical analysis wherein the concentration of glucose is the independent variable, and the set of values is the dependent variable, thereby determining the algorithm.

In a preferred embodiment, the compartment in the above-described methods is selected from the group consisting of a cellular, interstitial, lymphatic, bone, and blood compartment.

In another preferred embodiment, the compound in the above-described methods is selected from the group consisting of a fat, a protein, a glycoprotein, a lipoprotein, a carbohydrate, and a steroid. If the compound is a carbohydrate, glucose is a preferred compound.

By determining the concentration of a compound in different compartments within a part, a more accurate reading of the compound, either as a measure of the total amount of the compound, or as a corrected amount of the compound within a target compartment, is possible. This is especially true when the relative concentration of the compound varies within non-target compartments due to changes in the environment of the compartment, and an accurate reading of the compound in a target compartment, is required. The values determined of the compound in each compartment may be used to calculate the total amount of the compound in the body, they may be used as an indicator of the amount of compound within a compartment, or they may be used to calculate the amount of a compound in a target compartment This summary of the invention does not necessarily describe all necessary features of the invention but that the invention may also reside in a sub-combination of the described features.

DESCRIPTION OF PREFERRED EMBODIMENTS

The present invention relates to a method of measuring the concentration of a compound in the body of a subject, for example, a human or animal. More particularly, the present invention relates to a method of determining a concentration of a compound in a part of the subject, and optionally, of correlating the measured concentration of the compound to a specific clinical condition or to the propensity for a specific clinical condition.

The following description describes preferred embodiments by way of example only and without limitation to the combination of features necessary for carrying the invention into effect.

The expression "part of a subject", as used herein, refers to an element or section of a human or animal to which electromagnetic radiation (EMR) can be directed. The element or section can be, without limitation, an earlobe, a finger, an arm, a leg, torso, cheek, or a toe.

The term "compartment", as used herein, comprises a distinguishable portion of a tissue within a part of a human or animal. Examples of compartments, that are not to be considered limiting, include the vascular, interstitial, cellular, lymph, bone, and connective tissue, compartments. A compartment typically comprises fluid, for example, interstitial fluid, lymphatic fluid, the cytosol, and blood. Each of these compartments is capable of containing a biological compound such as, and without limitation to, a fat, a protein, a glycoprotein, a lipoprotein, a carbohydrate (e.g. glucose), and a steroid (e.g. cholesterol).

The present invention provides an apparatus for non-invasive determination of the concentration of one or more compounds within a part a subject. The apparatus comprises a receptor shaped so that it can be placed in contact with a region of skin from a subject. A source electromagnetic radiation (EMR) is fed into the receptor, and following interaction with one or more than one compounds within the body part, the EMR is collected and analyzed. The apparatus may be as known in the art, for example, but not limited to those disclosed in U.S. Pat. No. 5,361,758, WO 93/16629, U.S. Pat. No. 6,236,047 or 6,040,578 (all of which are incorporated herein by reference). The EMR that is collected after interaction with compounds within the part of the subject may be either reflected from, transmitted through, or both reflected from and transmitted through the part of the subject depending upon the apparatus used. The collected EMR signal is processed using one or more than one calibration algorithms to determine the concentration of one, or more than one target compounds within the target part.

In an aspect of the present invention, a part may be the skin, and the skin of a subject can be brought into contact with a receptor for measurement of one or more compounds within the skin. If a total analysis of compound is desired, a receptor may be placed, or pressed, against the skin and used to determine the concentration of a compound within all of the compartments of the skin. However, it may be desired that the blood content of the skin within the sample area be reduced, for example if the concentration of a compound in non-blood compartments is to be determined. If reduced blood content of the skin is desired, the skin may be lightly pressed in any suitable manner, for example, a portion of skin may be clamped or pressed by the receptor. The area of the skin of the subject that is most preferably clamped is an area that is readily drained of blood. Examples, which are not meant to be limiting in any manner, of such an area include loose skin, for example the skin on the wrist, the palm, the neck, or the lobe of the ear. Examples of a receptor that can clamp an appropriate area of skin include receptors shaped as tweezers, tongs, or as a vice or pin, such as a spring-clamp. However, as indicated above, other devices that fit over an arm or leg, or that accept a finger etc. may also be used as described herein.

A receptor of the present invention may also comprise a single sided probe that can make contact with a skin sample. Such a probe may comprise concentric rings of optic fibers so that each ring is made up by fibers carrying either input or output EMR. If the inner ring of fibers is carrying input EMR, then the outer ring of fibers may carry the output signal, or visa versa. This type of probe may be used to determine the concentration of a compound within the skin using reflectance. During use, the probe may be placed against the skin of the hand, arm, back or elsewhere.

Alternate configurations of an apparatus may also be used for the determination of a compound within a part, as described herein, including, but not limited to those described in U.S. Pat. No. 5,361,758, WO 93/16629, U.S. Pat. No. 6,236,047 or 6,040,578 (all of which are incorporated herein by reference). Modification of the calibration algorithms used to determine the concentration of one or more compounds of interest within each body part will be required so as to ensure that a compound within one, or more than one, particular compartment is determined.

The present invention provides a method to develop an algorithm that accounts for the differences in concentration of a compound within various compartments of a part of the body that lies along the light path emitted, and received by, the receptor or probe. For example, the concentration of a compound within each of the blood, the interstitial fluid, and the cellular compartment may be determined. using any suitable method for example, but not limited to direct measurement of the compound within each compartment, or by using non-invasive techniques, for example nuclear magnetic resonance, and determining the total concentration of the compound within the part of the body. From these values a reference measurement for the compound in the part of the body may be determined, and this reference value used to develop an algorithm for use in determining the concentration of the compound within a part of the body as described herein. Absorbance values of a part of a body may be obtained over a set of wavelengths set as a dependant variable, and glucose reference measurement used as an independent variable. These values can then be processed using any suitable statistical procedure, including but not limited to, Partial Least Squares or Multiple Linear Regression to produce an algorithm for the compound for a part of the body. This procedure can be repeated for any compound of interest, and for any part of the body, for which a body concentration of the compound is desired.

In the case of glucose, as an example, and which is not to be considered limiting, blood glucose levels can be readily determined using in vitro techniques as known in the art. The level of glucose in the interstitial compartment may be determined using reverse ionotophoesis (e.g. Tierney, M. J., et al. 2000, Electroanalysis 12:666; Potts, R. O. et al. 2002, Diabetes/Metabolism Research Reviews 18:s49-s53), Intercellular glucose concentrations may be determined using any suitable method, for example but not limited to microprobe analysis, for example using a microprobe (e.g. as available from MiniMed) to sample the glucose concentration within a cell. These values may then be used to determine a reference glucose value for the part of the body assayed.

The measurement of a compound within a part of a body may also change as a result of the change in volume of different compartments within the part of the body. This change in volume may either result in an underestimation or an over estimation of the concentration of the compound. For example, subkects with edama are characterized as having an increased interstitial volume. Therefore, in some instances, it may be desired to correct for changes in volume of the part of the body that is being sampled as described herein. In this instatnce, the volume of the part of the body may be determined prior to or during determination of the concentration of the compound within the part of the body. However, in many cases, the volume of the part of the body may be pre-determined and this value used as a constant with the algorithm in the determination of the concentration of a compound within a part of the body.

Therefore, the present invention provides a method for determining a concentration of a compound in a part of a subject, comprising:

(a) directing electromagnetic radiation (EMR) from the near-infrared spectrum onto the part;

(b) measuring a quantity of EMR reflected by, or transmitted through the part with a detector; and (c) performing a quantitative mathematical analysis of the quantity of EMR using an algorithm that accounts for concentration of the compound within more than one compartment, and the volume of the part; and (d) determining the concentration of the compound in the part.

The present invention also provides a method for determining the concentration of a compound in one or more than one compartments of a part of a human or animal, comprising:

(a) directing electromagnetic radiation (EMR) from the near-infrared spectrum onto the part;

(b) measuring a quantity of EMR reflected by, or transmitted through the part with a detector; and (c) performing a quantitative mathematical analysis of the quantity of EMR to determine the concentration of the compound in each of the different compartments of the part.

In order to more accurately determine the measurement of a compound of interest within a body part (as a total of all compartments), or to correct the measurement for the presence of the compound within each of the non-target compartments within the part, calibration algorithms specific for the compound within each compartment can be developed.

These compound-compartment specific algorithms may be used to either correct for the occurrence of the compound in a nontarget compartment, to ensure a proper estimation of the compound in all compartments, or both. Therefore, the present invention is also directed to providing algorithms for use within specific compartments. For example, which is not to be considered limiting in any manner, an algorithm may be developed for the determination of blood glucose, another algorithm for determining interstitial glucose, and another for cellular glucose.

The spectra of a compound may vary within different compartments due to the environment of the compound, or the relative concentration of the compound within the compartment. If the concentration of a compound within a compartment changes, or the relative amount of a compound changes with respect to other compounds within the compartment, the spectra of that compound may change. Without wishing to be bound by theory, such changes may arise from intermolecular associations, reduced molecular mobility, conformational changes and the like. Using this change in the spectral properties of a compound within each compartment, the occurrence of the compound within each compartment can be determined, and the relative contribution of the compound in each compartment, to the total amount of compound, can be analyzed.

In an average male, about 60% of the weight is water. In terms of volume, this is about 42 L, where about 23 L are intracellular and about 19 L are extracellular. Of the extracellular fluid, the plasma accounts for about 3 L and the interstitial fluid accounts for about 8 L. In summary, the largest fluid compartment contains the lowest glucose concentration. The proportion of fluid in the different compartments vary according to several factors including height, weight, age and gender. For an individual, variation occurs due to several factors including physical activity and hormone levels.

For example, which is not to be considered limiting in any manner, in the non-invasive determination of blood glucose concentration, levels of glucose within the interstitial compartment and vascular compartments are very similar due to rapid exchange of small molecules between these two compartments due to diffusion, but intracellular glucose is low because the glucose is readily metabolized. As glucose concentrations increase in blood, for example, when insulin levels are low or the effect of insulin is low, dehydration occurs as follows: When the blood glucose exceeds about 10 mmol/L, the kidney can no longer reabsorb the glucose, resulting in osmotic diuresis and a urine with elevated glucose concentration. The fluid is first lost from the vascular compartment, followed by the intistitial fluid, and finally the intracellular fluid—the body attempts to normalize the blood volume. The increase of glucose in non-target compartments can interfere with the measurement of blood glucose levels. Similarly, it may be desired to be able to determine an increase in interstitial glucose, or cellular glucose levels as an indicator of a medical condition, for example low insulin levels.

The present invention also provides a method for determining a corrected concentration of a compound in a compartment of a part of a subject, comprising:
  (a) directing electromagnetic radiation (EMR) from the near-infrared spectrum onto the part;
  (b) measuring a quantity of EMR reflected by, or transmitted through the part with a detector;
  (c) performing a quantitative mathematical analysis of the quantity of EMR using algorithms for the compound within each compartment; and
  (d) determining the corrected concentration of the compound in each compartment.

In an alternate embodiment, the relative increase or decrease in the concentration of a compound within a compartment may be determined by monitoring the change in a second metabolite (a marker analyte) that is known to change as a result of a modification within the compartment. For example, in the case of dehydration, dehydration-induced changes in a marker analyte alters the spectra of the analyte. These changes may arise due to conformational changes in the analyte, for example a protein, due to the changes in its aqueous environment, and associated intermolecular interactions (e.g. Carpenter J. F. et al., 1994, pp 134, in Cleland J., Langer R., eds. Formulation and Delivery of Protein and Peptides", Amer. Chem Soc.). Changes in the spectra of a marker analyte may then be used as an indicator of the dehydration state of the compartment, and the relative contribution of the compartment-specific effect of the compound of interests to the total measurement of the compound in the part, may then be determined.

Therefore, the present invention also provides a method for determining a corrected concentration of a compound in a part of a subject, comprising:
  (a) directing electromagnetic radiation (EMR) from the near-infrared spectrum onto the part;
  (b) measuring a quantity of EMR reflected by, or transmitted through the part with a detector;
  (c) performing a quantitative mathematical analysis of the quantity of EMR,
  (d) using an algorithm for a marker analyte and using a second algorithm for the compound, determining the concentration of the compound within the part; and
  (d) calculating the concentration of the compound within the part.

Preferred examples of compounds that are measured within a part, and within different compartments, according to the present invention are selected from the group consisting of fats, proteins, including cell-surface proteins, glycoproteins, lipoproteins, carbohydrates, and steroids. Preferably the compound is glucose, however, it is to be understood that the concentration of any desired compound may be determined within different compartments as described herein.

The present invention uses a correlation step to relate the measurements of transmitted or reflected light to a concentration value for one, or more than one, given compound in each of the compartments of a part of a subject. If desired, the measured concentration of the compound may be related to a particular parameter such as a clinical condition in need of treatment. The correlation steps used in the methods of this invention may involve several steps of linear regression analysis.

The concentration of a given compound is preferably calculated according to the present invention by using a calibration equation derived from a statistical analysis, for example but not limited to a least squares best fit, of a plot of the values of concentration of a calibration set of samples of the compound, which are determined using the method of the present invention, versus the values of the concentration of the calibration set measured directly by a different method. However, it is to be understood that other statistical tests may be used was known in the art, for example but not limited to multiple linear regression (MLR), partial least squares (PLS), and the like. Any known method for determining the concentration of one, or more than one, compound may be used as would be known to one of skill in the art.

The near infrared region of the electromagnetic spectrum is generally considered to be the spectral interval extending from 650 nm through to 2700 nm and measurements of samples as described herein are preferably taken in the about 700 nm to about 1100 nm range. Absorption bands observed in this interval are primarily the combination and overtone bands of the fundamental infrared bands. Although very weak in intensity, being typically less than one-tenth in intensity of the fundamental infrared bands, these bands are considered to be analytically useful because nearly all chemical species exhibit characteristic absorption bands in this spectral interval. The near infrared region is particularly well-suited to in vivo diagnostic applications because human tissue is essentially transparent to the incident radiation and therefore sufficient penetration of the radiation is possible to allow accurate quantitative analysis.

The source of EMR used in the present invention is preferably near-infrared light, for example but not limited to a polychromatic light source. This type of light source can emit light over a very wide bandwidth including light in the near infrared spectrum. In this case, the light from the light source preferably passes first through a collimator, which is a collection of lenses that concentrate the light into a narrow parallel beam directed at the receptor.

The polychromatic light source can be a quartz-halogen or a tungsten-halogen bulb and is powered by a stabilized power source, for example, a DC power supply, or by a battery. This polychromatic light source may be a tungsten-halogen lamp or it may be a collection of LEDs or other light sources selected to emit radiation in the range of about 650 to about 1100 nm.

A receptor is preferably used which is shaped to receive a part of the subject for sampling, for example a clamped part of the skin, or a finger. Alternatively, the receptor could be shaped so that the part of the human or animal, onto which the EMR is to be directed, is placed near the receptor rather than within the receptor. In any event, the sampled part of the skin should be in close contact with the receptor.

The EMR is directed onto, and dispersed by, a part of the subject. The dispersed light from the body part, either reflected, transmitted, or both, is collected by using any suitable method, for example, fiber optics, or lenses, and the output signal directed to a diffraction device that separates the wavelengths of light within the output signal into their component parts. Examples of a diffraction device include but are not limited to a diffraction grating or a holographic grating.

The collected signal can comprise EMR that has passed through a part of a subject, or has reflected off of a part of the subject, or a combination thereof. Preferably, the collected EMR has passed through the sample. The diffracting device preferably disperses the EMR into its component wavelengths so that the infrared region falls along the length of a detector such as, but not limited to a linear array detector (e.g. a 256 element photo diode array), or a CCD. In the case of an array, the detector has a series of diodes and is preferably electronically scanned by a microprocessor to measure the charge accumulated on each diode, the charge being proportional to the intensity of EMR for each wavelength transmitted through or reflected from the part of the subject in the receptor. The detector is connected to the microprocessor, producing an output spectrum, with the microprocessor analyzing the measurements and ultimately producing a result for each concentration level determined.

The result can be stored, shown on a display, or printed on a printer. A keyboard allows a user to control the device, for example, to specify a particular constituent to be measured. The timing and control is activated by the microprocessor to control the device, for example, to determine number and timing of measurements.

After measurements are obtained for the transmittance, reflectance or both, the log of the inverse of these measurements is preferably taken, that is, log 1/T and log 1/R, where T and R represent the transmittance and reflectance respectively. A reference set of measurements is taken of the incident light, being the light generated in the device when no part of the subject is in contact with the receptor. The absorbance is then calculated when a part of the subject is in contact with the receptor as a ratio of measurements compared to the reference set of measurements.

The second derivative of the measurements is preferably taken in order to reduce any variation in the result that will be caused by a change in path length for the light caused by measuring the compound concentration in different thicknesses of the parts of the subject. While there are other means of manipulating the data obtained from the measurements of reflectance and transmittance, which will produce the same results as those obtained by taking the second derivative, the taking of the second derivative is the preferred means.

As the results obtained can vary with the temperature of the part of the subject, the device used in the method of the present invention preferably contains a temperature sensor so that the temperature of the analyzed part can be measured rapidly at the time of the spectral sampling. This temperature sensor is typically a small-mass thermocouple. Computer software can then be used to allow the microprocessor to compensate for spectrum deviations due to the temperature. So as not to delay the production of results, the temperature sensor preferably has a 150 to 200 millisecond response time.

The linear array detector is preferably a photo diode array that is positioned to intercept, across its length, the dispersed spectrum from the diffraction grating. The microprocessor is directed by software to scan the linear array detector and calculate the second derivative of the spectrum computed. The microprocessor can then calculate the concentration of the particular constituents being measured using the absorbance and second derivative values for a number of selected wavelengths. A calibration equation is preferably used for each constituent and is determined by the compound being measured.

The use of the second derivative calculation also eliminates base line shifts due to different path lengths or absorbing water bands, and in addition, enhances the separation of overlapping absorption peaks of different constituents of the mixture being analyzed.

The microprocessor can collect up to one hundred spectra and can then immediately calculate the second derivative of the averaged results. Preferably, the results will be digitally displayed for the user. Also, by using the memory capacity of the microprocessor, a user can monitor trends by comparing the most recent result with previous results.

While the device of the present invention can be designed to measure one constituent, the device can also be designed to measure several constituents simultaneously.

The above description is not intended to limit the claimed invention in any manner, furthermore, the discussed combination of features might not be absolutely necessary for the inventive solution.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A method for determining a value of concentration of a compound in a part of a subject, consisting of:
   (a) directing electromagnetic radiation (EMR) from the near-infrared spectrum onto the part;
   (b) measuring a quantity of EMR reflected by, or transmitted through the part with a detector; and
   (c) determining the value of concentration of the compound in the part by performing a quantitative mathematical analysis of the quantity of EMR using only one algorithm that accounts for a value of concentration of the compound within each compartment of the part, and corrects the value of concentration of the compound within each compartment for changes in the volume of the part.

2. The method of claim 1, wherein the compound is selected from the group consisting of a fat, a protein, a glycoprotein, a lipoprotein, a carbohydrate, and a steroid.

3. The method of claim 1, wherein the compound is glucose.

* * * * *